United States Patent
Pan et al.

(10) Patent No.: US 10,143,678 B1
(45) Date of Patent: Dec. 4, 2018

(54) METHOD OF TREATMENT OF PREVENTING HYPERGLYCEMIA COMPLICATIONS

(71) Applicant: Sunway Biotech Co., LTD, Taipei (TW)

(72) Inventors: Tzu-Ming Pan, Taipei (TW); Chun-Lin Lee, Taitung County (TW); Ya-Wen Hsu, New Taipei (TW)

(73) Assignee: SUNWAY BIOTECH CO., LTD., Taipei (TW)

( * ) Notice: Subject to any disclaimer, the term of this patent is extended or adjusted under 35 U.S.C. 154(b) by 0 days.

(21) Appl. No.: 16/047,466

(22) Filed: Jul. 27, 2018

Related U.S. Application Data

(63) Continuation of application No. 15/246,549, filed on Aug. 25, 2016.

(30) Foreign Application Priority Data

Nov. 13, 2015 (TW) .............................. 104137535 A

(51) Int. Cl.
*A61K 36/00* (2006.01)
*A61K 31/366* (2006.01)
*A61K 36/062* (2006.01)
*A61K 36/06* (2006.01)
*A61K 36/8945* (2006.01)
*A61K 36/88* (2006.01)

(52) U.S. Cl.
CPC ............ *A61K 31/366* (2013.01); *A61K 36/06* (2013.01); *A61K 36/062* (2013.01); *A61K 36/88* (2013.01); *A61K 36/8945* (2013.01)

(58) Field of Classification Search
CPC ...................................................... A61K 36/00
See application file for complete search history.

(56) References Cited

U.S. PATENT DOCUMENTS

2010/0278983 A1    11/2010  Pan et al.

OTHER PUBLICATIONS

Shi et al., "Anti-diabetic Effects of Monascus Purpureus NTU 568 Fermented Products on Streptozotocin-Induced Diabetic Rats". Institute of Microbiology and Biochemistry. Journal of Agricultural and Food Chemistry (2010), 58(13), 7634-7640. American Chemical Society.
Holland., "Hyperglycemia and Type 2 Diabetes". My Way With Type 2 Diabetes. Aug. 3, 2016. Healthline.
Bledsoe. "Type 2 Diabetes and Fatty Liver Disease". Mar. 27, 2016. Everyday Health.

*Primary Examiner* — Qiuwen Mi
(74) *Attorney, Agent, or Firm* — Anova Law Group, PLLC

(57) ABSTRACT

Disclosures of the present invention describe a method of treatment of preventing hyperglycemia complications using at least one pharmaceutical made from a red mold product, wherein the red mold product is a red mold rice or a red mold *Dioscorea*, and the pharmaceutical is an extract obtained from the red mold product. Particularly, the extract can be Monascin, Ankaflavin, or a combination of Monascin and Ankaflavin. Moreover, a variety of experiment data have proved that the extract indeed exhibits a prevention effect in hyperglycemia complications comprising non-alcoholic liver damage and kidney failure.

3 Claims, 11 Drawing Sheets

METHOD OF TREATMENT OF PREVENTING HYPERGLYCEMIA COMPLICATIONS

CROSS-REFERENCE TO RELATED APPLICATIONS

This application is a Continuation Application of U.S. patent application Ser. No. 15/246,549, filed on Aug. 25, 2016, entitled with "Composition for Regulating Blood Sugar", which is hereby incorporated herein by reference.

BACKGROUND OF THE INVENTION

1. Field of the Invention

The present invention relates to the technology field of therapeutic applications of pharmaceutical materials, and more particularly to a method of treatment of preventing hyperglycemia complications using the extractions obtained from *Monascus*-fermented products.

2. Description of the Prior Art

American Diabetes Association (FDA) has published the way to judge whether a person suffers from a diabetes mellitus (DM) or not. The person would be diagnosed with diabetes mellitus in the case of that his fasting blood glucose (GLU-AC) concentration is higher than 126 mg/dL or his 2 hours postprandial blood glucose (2hPBG) concentration exceeds 200 mg/dL. On the other hand, the person is diagnosed with Impaired Glucose Tolerance (IGT) as the measurement value of GLU-AC thereof falls in a range between 100 mg/dL and 126 mg/dL or his 2hPBG is measured to fall in a range from 140 mg/dL to 200 mg/dL. IGT means that blood glucose is raised beyond normal levels, but not high enough to warrant a diabetes diagnosis.

One of key factors to induce the occurrence of diabetes mellitus and metabolism syndrome is Reactive Oxygen Species (ROS) resulted from Hyperglycemia. Moreover, ROS is also found to participate in the dysfunction of β-cell of pancreas. In addition, insulin resistance often progresses to full Type 2 diabetes mellitus (T2DM) or latent autoimmune diabetes of adults. Insulin resistance is commonly produced when Hyperglycemia develops after a meal and the pancreatic β-cells are unable to supply sufficient insulin to maintain normal blood sugar levels. Insulin resistance also decreases the translocation of glucose transporters (GLUT) to the cell membrane. Consequently, Type 2 diabetes or latent autoimmune diabetes occurs in the case of glucose levels becoming higher throughout the day as the resistance increases and compensatory insulin secretion fails.

The statistical data collected by Ministry of Health and Welfare of Taiwan have reported that 90% T2DM patients would simultaneously suffer from obesity. The adipose tissue of an obesity patient may releases inflammation factors such as hypoxia-inducible factor 1α (HIF-1α), tumor necrosis factor-α (TNF-α) and interleukin (IL), wherein the excessive amount of inflammation factors would induce lipolysis action to produce a large amount of glycerin and free fatty acid (FFA), so as to aggravate the production of Hyperglycemia, fatty liver, and high blood ketone. Moreover, not only impelling the production of inflammation factors and ROS, FFA also inhibits the activity of insulin receptor by activating diacylglycerol (DAG) and protein kinasenk C (PKC), so as to result in the occurrence of insulin resistance.

Conventionally-used blood sugar reducing drugs are known including: non-sulfonylurea insulin secretagogue, sulfonylurea insulin secretagogue, biguanides, alpha-glucohydrolase inhibitor, and DPP-4 inhibitor (inhibitor of dipeptidyl peptidase 4). However, all the above-mentioned blood sugar reducing drugs have side-effects with varying severity, such as diarrhea, anorexia, nausea, and fatal lactic acidosis.

Insulin sensitizers are also the conventionally-used blood sugar reducing drugs, including troglitazone, rosiglitazone and pioglitazone. The insulin sensitizer possesses anti-diabetic activity through activation of a nuclear receptor called PPARγ (Peroxisome proliferator-activated receptor γ). However, over-activation of PPARγ drives the unwanted and often unacceptable side effects associated with the currently-approved insulin sensitizers, such as edema, weight gain, congestive heart failure, hepatotoxicity.

Thus, because the conventionally-used blood sugar reducing drugs may cause side-effects to DM patients, the inventor of the present application has made great efforts to make inventive research thereon and eventually provided a method of treatment of preventing hyperglycemia complications.

SUMMARY OF THE INVENTION

The primary objective of the present invention is to provide a method of treatment of preventing hyperglycemia complications using at least one pharmaceutical made from a red mold product, wherein the red mold product is a red mold rice or a red mold *Dioscorea*, and the pharmaceutical is an extract obtained from the red mold product. Particularly, the extract can be Monascin, Ankaflavin, or a combination of Monascin and Ankaflavin. Moreover, a variety of experiment data have proved that the extract indeed exhibits a prevention effect in hyperglycemia complications comprising non-alcoholic liver damage and kidney failure.

In order to achieve the primary objective of the present invention, the inventor of the present invention provides a first embodiment of the method of treatment of preventing hyperglycemia complications, wherein the hyperglycemia complications comprises non-alcoholic liver damage and kidney failure, and the method comprising administering to an adult once-daily 3.0 mg Monascin.

Moreover, for achieving the primary objective of the present invention, the inventor of the present invention provides a second embodiment of the method of treatment of preventing hyperglycemia complications, wherein the hyperglycemia complications comprises non-alcoholic liver damage and kidney failure, and the method comprising administering to an adult once-daily 1.5 mg Ankaflavin.

In addition, for achieving the primary objective of the present invention, the inventor of the present invention provides a third embodiment of the method of treatment of preventing hyperglycemia complications, wherein the hyperglycemia complications comprises non-alcoholic liver damage and kidney failure, and the method comprising administering to an adult once-daily a 4.5 mg composition comprising 3.0 mg Monascin and 1.5 mg Ankaflavin.

BRIEF DESCRIPTION OF THE DRAWINGS

The invention as well as a preferred mode of use and advantages thereof will be best understood by referring to the following detailed description of an illustrative embodiment in conjunction with the accompanying drawings, wherein.

DETAILED DESCRIPTION OF THE PREFERRED EMBODIMENTS

Figure 1:
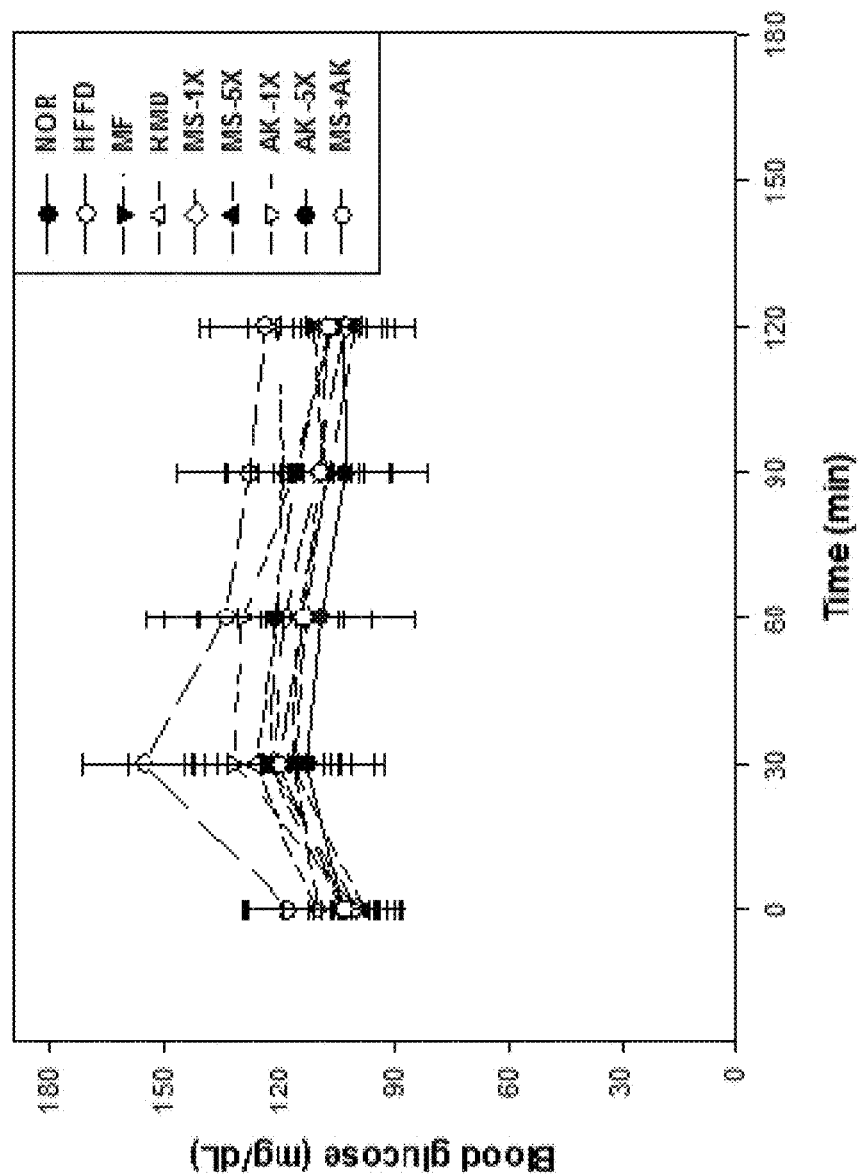
FIG. 1 shows a curve plot of time versus blood glucose.

To more clearly describe a method of treatment of preventing hyperglycemia complications according to the present invention, embodiments of the present invention will be described in detail with reference to the attached drawings hereinafter.

It is well known that *Monascus* species is divided into *Monascus pilosus*, *Monascus purpureus*, *Monascus ruber*, *Monascus floridanus*, *Monascus pallens*, and *Monascus sanguineus*. Moreover, according to culture patterns, growth patterns, olors, and cleistothecia colors, the *Monascus* species is further divided into *Monascus pilosus*, *Monascus purpureus*, and *Monascus ruber*.

The present invention provides a method of treatment of preventing hyperglycemia complications using at least one pharmaceutical made from a red mold product, wherein the red mold product is a red mold rice or a red mold *Dioscorea*, and the pharmaceutical is an extract obtained from the red mold product. The extract is Monascin, Ankaflavin, or a combination of Monascin and Ankaflavin. It is worthwhile to further explain that, the red mold product is produced by inoculating a *Monascus purpureus* NTU 568 to a substrate and then applying culturing and drying process to the inoculated substrate. The process steps for producing the red mold product such as red mold rice (RMR) or red mold *Dioscorea* (RMD) are fully disclosed by U.S. Pat. No. 9,358,221. Moreover, in order to verify the practicability of the method of treatment of preventing hyperglycemia complications proposed by the present invention, a particularly-arranged of animal experiment is completed by inventors. After 1-week pre-feeding, several SD rats are divided into 9 experimental groups for carrying out 10-week animal experiment.

First of the 9 experimental groups is NOR group consisting of 8 SD rats, wherein the "NOR" means that the SD rats are fed with normal diet. During the animal experiment, the SD rats in NOR group are fed with cornstarch diet unlimitedly. Moreover, RO water is adopted as the test sample for orally administering to SD rats in NOR group through feeding tubes. Second of the 9 experimental groups is HFFD group consisting of 8 SD rats, wherein the "HFFD" means the SD rats are fed with high fat and fructose diet. During the animal experiment, the SD rats in HFFD group are fed with chew diet consisting of 73.3% corn starch and 26.7% butter powder.

Third of the 9 experimental groups is MF group consisting of 8 SD rats, wherein the "MF" means that drug of Metformin is used as the test sample for orally administering to SD rats in MF group through feeding tubes. Moreover, during the animal experimental, the SD rats in MF group are fed with high fat and fructose diet unlimitedly. Fourth of the 9 experimental groups is RMD group consisting of 8 SD rats, wherein the "RMD" means that powder of red mold *Dioscorea* (RMD) is taken as test sample for orally administering to SD rats in RMD group through feeding tubes. Moreover, during the animal experimental, the SD rats in RMD group are fed with high fat and fructose diet unlimitedly.

Fifth of the 9 experimental groups is MS1X group consisting of 8 SD rats, wherein the "MS1X" means that 1-fold dosage of Monascin is used as the test sample for orally administering to SD rats in MS1X group through feeding tubes. Moreover, during the animal experimental, the SD rats in MS1X group are fed with high fat and fructose diet unlimitedly. Sixth of the 9 experimental groups is MS5X group consisting of 8 SD rats, wherein the "MS5X" means that 5-fold dosage of Monascin is taken as the test sample for orally administering to SD rats in MS5X group through feeding tubes. Moreover, during the animal experimental, the SD rats in MS5X group are fed with high fat and fructose diet unlimitedly.

Seventh of the 9 experimental groups is AK1X group consisting of 8 SD rats, wherein the "AK1X" means that 1-fold dosage of Ankaflavin is taken as the test sample for orally administering to SD rats in AK1X group through feeding tubes. Moreover, during the animal experimental, the SD rats in AK1X group are fed with high fat and fructose diet unlimitedly. Eighth of the 9 experimental groups is AK5X group consisting of 8 SD rats, wherein the "AK5X" means that 5-fold dosage of Ankaflavin is taken as the test sample for orally administering to SD rats in AK5X group through feeding tubes. Moreover, during the animal experimental, the SD rats in AK5X group are fed with high fat and fructose diet unlimitedly.

The last one of the 9 experimental groups is MS-AK group consisting of 8 SD rats, wherein the "MS-AK" means that a combination of 1-fold-dose Ankaflavin and 1-fold-dose Monascin is taken as the test sample for orally administering to SD rats in MS-AK group through feeding tubes. Moreover, during the animal experimental, the SD rats in MS-AK group are fed with high fat and fructose diet unlimitedly. Herein, it needs to particularly explain that, the dosage for the above-mentioned different test samples are integrated in following Table 1.

TABLE 1

| Group | Test sample | Rat dosage (mg/kg*bw/day) | Adult dosage (mg/day) |
|---|---|---|---|
| NOR | RO water | — | — |
| HFFD | RO water | — | — |
| MF | Metformin | 78.06 | 500 |
| RMD | Red mold dioscorea | 104.17 | 1000 |
| MS1X | Monascin | 0.31 | 3 |
| MS5X | Monascin | 1.56 | 15 |
| AK1X | Ankaflavin | 0.16 | 1.5 |
| AK5X | Ankaflavin | 0.78 | 7.5 |

TABLE 1-continued

| Group | Test sample | Rat dosage (mg/kg*bw/day) | Adult dosage (mg/day) |
|---|---|---|---|
| MS-AK | Monascin + Ankaflavin | 0.31 + 0.16 | 3 + 1.5 |

The rat dosage for different test samples used in the 9 groups can be easily calculated by using following rat-adult dosage transforming equation: rat dosage=(adult dosage/60 kg)*6.25.

Please refer to following Table 2. Because the high fat and fructose diet is consisted of 73.3% corn starch and 26.7% butter powder, the calorie obtained by the rats in 9 groups can be easily estimated. Moreover, the rats' weight data are recorded in following Table 3 after executing the animal experiment for 10 days.

TABLE 2

| Group | Intake diet (g/day/rat) | Intake water (mL/day/rat) | Daily intake calorie (kcal/day/rat) |
|---|---|---|---|
| NOR | $23.95 \pm 0.74^c$ | $48.05 \pm 3.45^c$ | $80.00 \pm 2.48^a$ |
| HFFD | $15.76 \pm 1.29^b$ | $31.58 \pm 1.17^{ab}$ | $104.82 \pm 7.69^c$ |
| MF | $14.78 \pm 1.72^{ab}$ | $32.44 \pm 3.72^{ab}$ | $98.38 \pm 6.94^{ab}$ |
| RMD | $14.21 \pm 1.44^a$ | $32.63 \pm 3.46^{ab}$ | $98.16 \pm 7.10^b$ |
| MS1X | $14.46 \pm 1.18^{ab}$ | $33.79 \pm 1.79^b$ | $98.53 \pm 5.03^{bc}$ |
| MS5X | $14.37 \pm 1.76^{ab}$ | $33.57 \pm 3.47^b$ | $97.91 \pm 8.17^{bc}$ |
| AK1X | $14.85 \pm 0.84^{ab}$ | $32.21 \pm 2.57^{ab}$ | $99.85 \pm 4.25^{bc}$ |
| AK5X | $14.08 \pm 1.75a$ | $32.21 \pm 2.63^{ab}$ | $102.17 \pm 7.44^{bc}$ |
| MS-AK | $14.48 \pm 0.90^{ab}$ | $29.79 \pm 1.27^a$ | $96.26 \pm 5.02^b$ |

TABLE 3

| Group | Daily intake calorie (kcal/day/rat) | Weight (g) |
|---|---|---|
| NOR | $80.00 \pm 2.48^a$ | $232.00 \pm 21.33^a$ |
| HFFD | $104.82 \pm 7.69^c$ | $296.25 \pm 45.3^b$ |
| MF | $98.38 \pm 6.94^{ab}$ | $268.75 \pm 36.22^{ab}$ |
| RMD | $98.16 \pm 7.10^b$ | $292.75 \pm 44.84^b$ |
| MS1X | $98.53 \pm 5.03^{bc}$ | $285.75 \pm 34.34^b$ |
| MS5X | $97.91 \pm 8.17^{bc}$ | $275.13 \pm 49.48^b$ |
| AK1X | $99.85 \pm 4.25^{bc}$ | $278.38 \pm 22.03^b$ |
| AK5X | $102.17 \pm 7.44^{bc}$ | $262.25 \pm 42.85^{ab}$ |
| MS-AK | $96.26 \pm 5.02^b$ | $274.59 \pm 19.89^b$ |

From the data shown in Table 2 and Table 3, it can find that, the daily intake calorie of the rats of all experimental groups are obviously higher than the daily intake calorie of the rats in the NOR group. Moreover, comparing to the rats of HFFD group, the daily intake calorie of the rats in RMD, MS5X, and MS-AK group are lower. In addition, it can also find that, the weight of the rats of all experimental groups are obviously heavier than the weight of the rats in the NOR group. Moreover, comparing to the rats of HFFD group, the weight of the rats in MF, RMD, MS1X, MS5X, AK1X, AK5X, and MS-AK group are lighter.

Blood Sugar Regulating Effects on SD Rats Provided by the Different Test Samples Before evaluating the blood sugar regulating ability of the different test samples, 12-hour fast must be executed on the rats of the 9 experimental groups. After that, blood for determining the concentration of fasting blood glucose (GLU-AC) is collected from the rats's orbital by using capillary tubes. On the other hand, to carry out oral glucose tolerance test (OGTT), the rats in the 9 experimental groups are orally administered with a glucose solution when starting the 12-hour fast; and then, the rats has their blood tested again 30 minutes, 60 minutes and 90 minutes after drinking the glucose solution.

Figure 2:
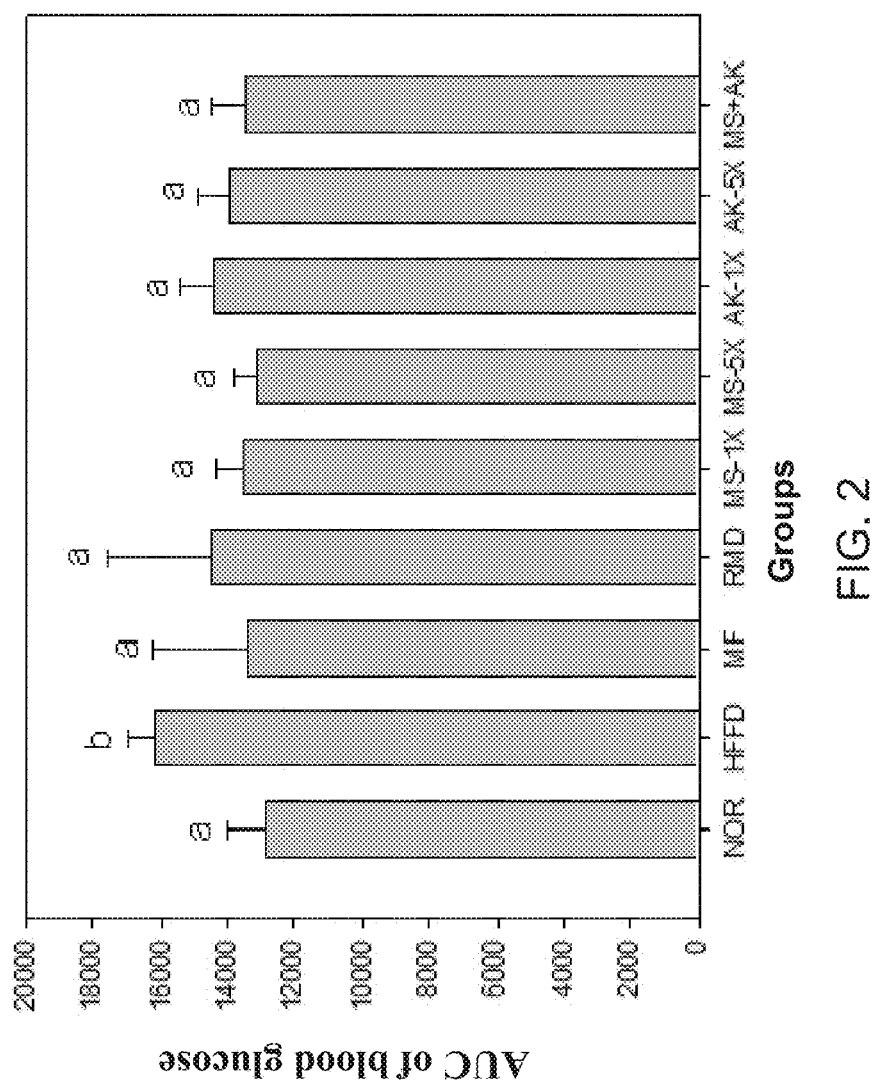
FIG. 2 shows a statistical bar graph of group versus AUC (area under curve) of blood glucose.

Please refer to FIG. 1, where a curve plot of time versus blood glucose. Moreover, please refer to FIG. 2, which provides a statistical bar graph of group versus AUC (area under curve) of blood glucose. From FIG. 1, it can easily find that, the glucose levels of the rats in HFFD group are largely higher than the glucose levels of the rats in NOR group at 0 and 30 minutes. On the other hand, from FIG. 2, it is able to know that the rats in HFFD group have been suffered from Hyperglycemia because the AUC (area under curve) value of HFFD group is higher than the AUC value of NOR group. However, all the AUC values of MF, MS1X, MS5X, AK5X, and MS-AK group are obviously lower than the HFFD group's AUC value. Moreover, the experimental data of FIG. 2 also prove that the 5-fold-dose Ankaflavin shows better AUC reducing ability. Herein, it is worth noting that, although the combination of 1-fold-dose Ankaflavin and 1-fold-dose Monascin as well as 1-fold-dose Ankaflavin cannot largely lower the AUC value, the AUC values of RMD group and AK1X group are still lower than the HFFD group's AUC value.

Therefore, it is able to assume the cause resulted in the occurrence of Hyperglycemia in the rats of HFFD group is that the glucose cannot be effectively utilized due to the failure of insulin receptors, wherein the failure of insulin receptors is caused by a large amount of adipocytes accumulation. However, according to the experimental data provided by FIG. 1 and FIG. 2, the blood glucose concentrations of the rats fed with Monascin and/or Ankaflavin are effectively regulated. Such result implies that the insulin receptors in the rats fed with Monascin and/or Ankaflavin work normally for receiving insulin.

In normal situation, beta cells of pancreas would start to produce insulin after the rats eat high energy diets. However, insulin resistance (IR) may be induced in the rats of HFFD group because the beta cells are killed by ROS (Reactive oxygen species) induced by Hyperglycemia. Based on above reasons, it needs to observe the effects provided by the different test samples on the GLU-AC, insulin, insulin resistance, and Fructosamine of the rats.

The blood collected by capillary tubes are disposed into a 2-mL microcentrifuge tube. After staying for 5 minutes, the microcentrifuge tube carrying with blood is treated with a centrifugation process, and then the serum of the blood is stored in an environment with −80° C. In this animal experiment, insulin determination is carried out by dropping the serum onto an enzyme-linked immunosorbent assay (ELISA) insulin kit. Thereafter, the insulin resistance is then calculated by using following equation: HOMA-IR=[insulin (µU/mL)*glucose (mmol/L)]/22.5. On the other hand, insulin determination is completed by dropping the serum onto a fructosamine assay kit. Therefore, the determination data of blood glucose, insulin, insulin resistance, and fructosamine are recorded and integrated in following Table 4 and Table 5.

TABLE 4

| Group | Blood glucose (mg/dL) | Insulin (µU/mL) |
|---|---|---|
| NOR | $95.91 \pm 8.52^{ab}$ | $40.04 \pm 0.35^a$ |
| HFFD | $121.11 \pm 4.96^c$ | $55.60 \pm 5.06^c$ |
| MF | $102.38 \pm 12.03^{ab}$ | $41.55 \pm 1.09^a$ |
| RMD | $105.63 \pm 11.51^b$ | $43.93 \pm 5.43^{ab}$ |

TABLE 4-continued

| Group | Blood glucose (mg/dL) | Insulin (μU/mL) |
|---|---|---|
| MS1X | 100.25 ± 4.59$^{ab}$ | 43.12 ± 3.95$^{ab}$ |
| MS5X | 95.50 ± 6.00$^{a}$ | 40.45 ± 0.60$^{a}$ |
| AK1X | 98.38 ± 11.01$^{ab}$ | 46.52 ± 5.24$^{b}$ |
| AK5X | 97.38 ± 9.20$^{ab}$ | 45.73 ± 3.49$^{b}$ |
| MS-AK | 99.51 ± 5.81$^{ab}$ | 41.35 ± 1.52$^{a}$ |

TABLE 5

| Group | Insulin resistance | Fructosamine (mM) |
|---|---|---|
| NOR | 10.10 ± 0.7$^{a}$ | 0.71 ± 0.05$^{a}$ |
| HFFD | 15.71 ± 1.85$^{c}$ | 1.32 ± 0.12$^{d}$ |
| MF | 10.69 ± 1.08$^{ab}$ | 0.88 ± 0.06$^{c}$ |
| RMD | 12.01 ± 1.47$^{b}$ | 0.91 ± 0.09$^{c}$ |
| MS1X | 10.96 ± 1.3$^{ab}$ | 0.87 ± 0.07$^{c}$ |
| MS5X | 9.77 ± 0.7$^{a}$ | 0.84 ± 0.06$^{bc}$ |
| AK1X | 11.99 ± 2.08$^{b}$ | 0.90 ± 0.06$^{c}$ |
| AK5X | 11.89 ± 1.78$^{b}$ | 0.88 ± 0.06$^{c}$ |
| MS-AK | 10.70 ± 1.24$^{ab}$ | 0.80 ± 0.06$^{ab}$ |

From Table 4, it can easily find that, the GLU-AC concentration of the rats in HFFD group is greater than the GLU-AC concentration of the rats in NOR group. However, comparing to the rats of HFFD group, the GLU-AC concentrations of the rats in MF, RMD, MS1X, MS5X, AK1X, AK5X, and MS-AK group are largely lowered. Moreover, it is worth noting that, the GLU-AC level of the rats in MS5X group is almost equal to the GLU-AC level of the rats in NOR group. Such result implies that the 5-fold-dose Monascin possesses high-efficiency blood sugar regulating ability.

From Table 4, it can also find that, the insulin concentration of the rats in HFFD group is greater than the insulin concentration of the rats in NOR group. However, comparing to the rats of HFFD group, the insulin concentrations of the rats in MF, RMD, MS1X, MS5X, AK1X, AK5X, and MS-AK group are largely lowered. Moreover, it is worth noting that, the insulin level of the rats in MS5X group is almost equal to the insulin level of the rats in NOR group. Such result implies that the 5-fold-dose Monascin possesses high-efficiency insulin regulating ability.

Moreover, from Table 5, it can easily find that, the insulin resistance value of the rats in HFFD group is greater than the insulin resistance value of the rats in NOR group. However, comparing to the rats of HFFD group, the insulin resistance value of the rats in MF, RMD, MS1X, MS5X, AK1X, AK5X, and MS-AK group are largely lowered. Moreover, it is worth noting that, the insulin resistance value of the rats in MS5X group is almost equal to the insulin resistance value of the rats in NOR group. Such result implies that the 5-fold-dose Monascin possesses high-efficiency insulin resistance value lowering ability.

From Table 5, it can also find that, the fructosamine concentration of the rats in HFFD group is greater than the fructosamine concentration of the rats in NOR group. However, comparing to the rats of HFFD group, the fructosamine concentration of the rats in MF, RMD, MS1X, MS5X, AK1X, AK5X, and MS-AK group are largely lowered. So that, the experimental data provided by Table 4 and Table 5 prove that the Monascin and Ankaflavin indeed possess functionality to regulate blood glucose, insulin, insulin resistance, and fructosamine.

Particular Effects Provided by Different Test Samples on Liver and Kidney of SD Rats Insulin is used for impelling the absorption and utilization of blood glucose in liver, muscle and adipose tissue. Because white adipose tissue (WAT) is used for storing triglycerides (TG) transformed from blood glucose, a large amount of accumulation of adipocytes would cause the occurrence of inflammatory response so as to induce lipolysis action. Therefore, the inflammatory-induced lipolysis action would produce a large amount of glycerin and free fatty acid (FFA), so as to aggravate the production of Hyperglycemia, fatty liver, and high blood ketone. Based on above reasons, the effects provided by the different test samples on liver, kidney, and adipose tissue weight of the rats are needed to be determined.

For carrying out the determination of liver, kidney, and adipose tissue weight, it needs to sacrifice the rats. After sacrificing the rat, blood to be determined is collected from the intraperitoneal of the rat by using syringes, and then the collected blood are disposed into a 2-mL microcentrifuge tube. After staying for 5 minutes, the microcentrifuge tube carrying with blood is treated with a centrifugation process, and then the serum of the blood is stored in an environment with −20° C. After that, the liver, kidney, and adipose tissue are taken out of the rat.

Following Table 6 has recorded with weight data of the liver and kidney tissue. From Table 6, it can easily find that, the liver weights of the rats in HFFD group are largely higher than the liver weights of the rats in NOR group. However, comparing to the rats of HFFD group, the liver weights of the rats in MF, RMD, MS1X, MS5X, AK1X, AK5X, and MS-AK group are largely lowered. Herein, it is worth noting that, the liver weight data of the rats in MS5X group is almost equal to the liver weight data of the rats in NOR group. Such result implies that the 5-fold-dose Monascin possesses high-efficiency liver weight regulating ability.

TABLE 6

| Group | Liver weight | Kidney weight |
|---|---|---|
| NOR | 13.67 ± 1.07$^{a}$ | 3.78 ± 0.16$^{a}$ |
| HFFD | 22.08 ± 2.09$^{d}$ | 3.42 ± 0.26$^{b}$ |
| MF | 15.61 ± 1.53$^{bc}$ | 3.64 ± 0.26$^{ab}$ |
| RMD | 16.47 ± 1.85$^{c}$ | 3.62 ± 0.20$^{ab}$ |
| MS1X | 15.25 ± 1.64$^{bc}$ | 3.61 ± 0.20$^{ab}$ |
| MS5X | 14.62 ± 1.84$^{ab}$ | 3.71 ± 0.40$^{ab}$ |
| AK1X | 15.36 ± 1.09$^{bc}$ | 3.72 ± 0.31$^{ab}$ |
| AK5X | 15.58 ± 1.32$^{bc}$ | 3.55 ± 0.29$^{ab}$ |
| MS-AK | 15.70 ± 1.00$^{bc}$ | 3.58 ± 0.25$^{ab}$ |

Following Table 7 has recorded with weight data of the peri-adrenal and epididymal adipose tissue. From Table 7, it can easily find that, the weights of peri-adrenal and epididymal adipose tissue of the rats in HFFD group are largely higher than the weights of peri-adrenal and epididymal adipose tissue of the rats in NOR group. However, comparing to the rats of HFFD group, the weights of peri-adrenal and epididymal adipose tissue of the rats in MF, RMD, MS1X, MS5X, AK1X, AK5X, and MS-AK group are largely lowered.

TABLE 7

| Group | Percentage of weight of peri-adrenal adipose tissue (%) | Percentage of weight of epididymal adipose tissue (%) | Occupying percentage of summation of the weights of peri-adrenal and epididymal adipose tissue in body Fat (%) |
|---|---|---|---|
| NOR | 1.39 ± 0.24$^{a}$ | 1.11 ± 0.15$^{a}$ | 2.54 ± 0.38$^{a}$ |
| HFFD | 3.61 ± 0.47$^{c}$ | 2.26 ± 0.46$^{c}$ | 5.88 ± 0.82$^{c}$ |
| MF | 3.33 ± 0.66$^{bc}$ | 1.83 ± 0.43$^{b}$ | 4.27 ± 1.43$^{bc}$ |

TABLE 7-continued

| Group | Percentage of weight of peri-adrenal adipose tissue (%) | Percentage of weight of epididymal adipose tissue (%) | Occupying percentage of summation of the weights of peri-adrenal and epididymal adipose tissue in body Fat (%) |
|---|---|---|---|
| RMD | 3.04 ± 0.65$^b$ | 1.95 ± 0.39$^{bc}$ | 4.98 ± 0.50$^c$ |
| MS1X | 2.99 ± 0.60$^b$ | 1.97 ± 0.33$^{bc}$ | 5.12 ± 0.84$^{bc}$ |
| MS5X | 3.15 ± 0.45$^{bc}$ | 1.79 ± 0.33$^b$ | 4.97 ± 0.80$^{bc}$ |
| AK1X | 2.75 ± 0.37$^b$ | 1.96 ± 0.4$^{bc}$ | 4.32 ± 0.59$^b$ |
| AK5X | 2.96 ± 0.43$^b$ | 1.69 ± 0.3$^b$ | 4.30 ± 0.53$^b$ |
| MS-AK | 2.99 ± 0.60$^b$ | 2.02 ± 0.39$^{bc}$ | 5.06 ± 0.43$^{bc}$ |

The high fat and fructose diet may also cause the rats suffer from Hypertriglyceridemia, so as to damage the liver. Following Table 8 has recorded with data of triglycerides (TG) and total cholesterol (TC). From Table 8, it can easily find that, the concentrations of triglycerides and total cholesterol of the rats in HFFD group are largely higher than the concentrations of triglycerides and total cholesterol of the rats in NOR group. However, comparing to the rats of HFFD group, the concentrations of triglycerides and total cholesterol of the rats in MF, RMD, MS1X, MS5X, AK1X, AK5X, and MS-AK group are largely lowered.

TABLE 8

| Group | TG (mg/dL) | TC (mg/dL) |
|---|---|---|
| NOR | 82.25 ± 7.85$^a$ | 75.00 ± 7.5$^b$ |
| HFFD | 255.00 ± 37.01$^e$ | 84.50 ± 11.88$^c$ |
| MF | 170.88 ± 46.04$^d$ | 68.50 ± 9.93$^{ab}$ |
| RMD | 139.13 ± 39.3$^{cd}$ | 73.00 ± 10.10$^{ab}$ |
| MS1X | 136.63 ± 29.66$^{cd}$ | 70.00 ± 2.88$^{ab}$ |
| MS5X | 99.88 ± 18.90$^{ab}$ | 66.75 ± 7.11$^{ab}$ |
| AK1X | 138.75 ± 47.07$^{cd}$ | 66.50 ± 7.87$^{ab}$ |
| AK5X | 137.63 ± 33.21$^{cd}$ | 64.25 ± 8.94$^a$ |
| MS-AK | 129.88 ± 18.15$^{bc}$ | 64.63 ± 6.39$^a$ |

So that, the experimental data provided by Table 6, Table 7 and Table 8 prove that the Monascin and Ankaflavin indeed possess functionality to lower insulin resistance by regulating insulin, so as to reduce the liver, kidney and adipose tissue weight. Moreover, the Monascin and Ankaflavin also possess functionality to lower the TG level in adipose tissue by regulating blood glucose concentration.

On the other hand, in normal situation, human serum would include adiponectin of 5-30 μg/mL for maintaining the balance between glucose and lipids. Adiponectin dose not only play an important role in the formation of insulin resistance, but also has close relationship with TG.

Figure 3:
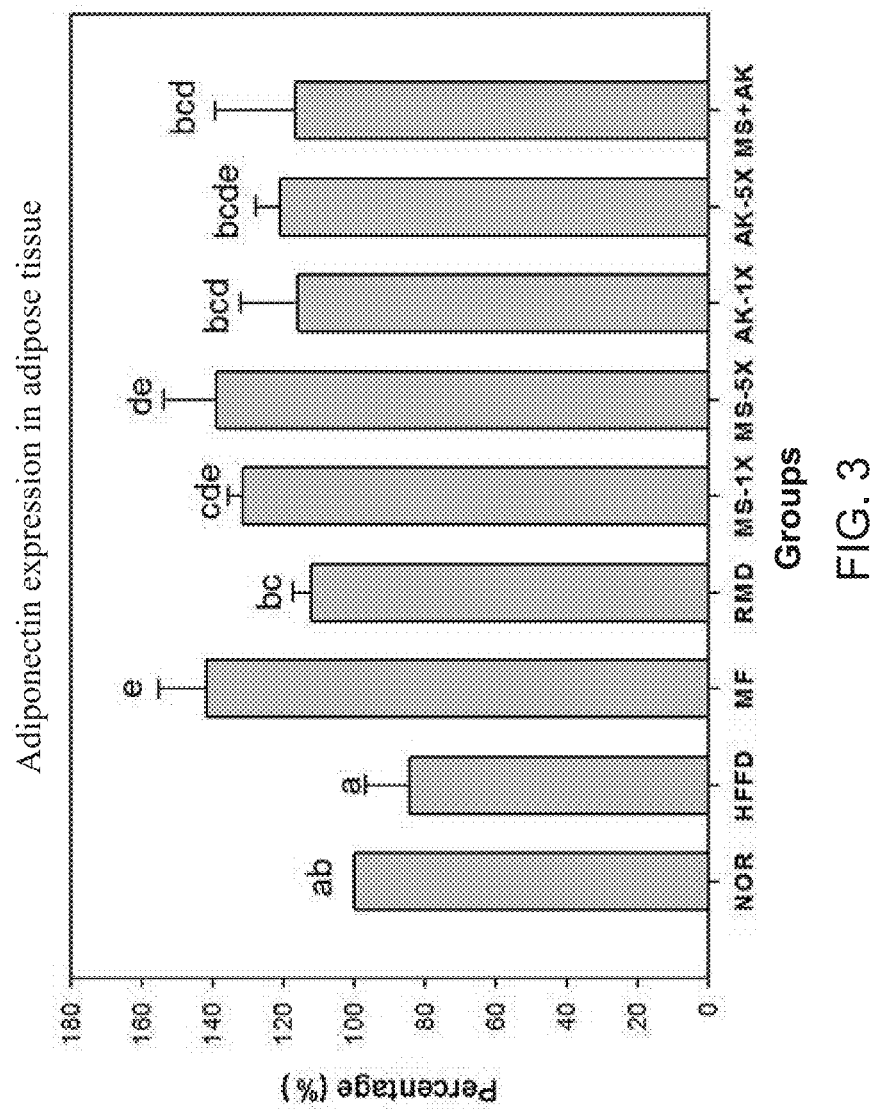
FIG. 3 shows a statistical bar graph of adiponectin expression in adipose tissue.

Please refer to FIG. 3, which provides a statistical bar graph of adiponectin expression in adipose tissue. From Table FIG. 3, it can easily find that, the percentage of adiponectin expression of the rats in HFFD group is lower than the percentage of adiponectin expression of the rats in NOR group. However, comparing to the rats of HFFD group, the percentage of adiponectin expression of the rats in MF, RMD, MS1X, MS5X, AK1X, AK5X, and MS-AK group is largely enhanced. So that, the experimental data provided by FIG. 3 prove that the Monascin and Ankaflavin indeed possess functionality to regulate the adiponectin level in adipose tissue.

Figure 4:
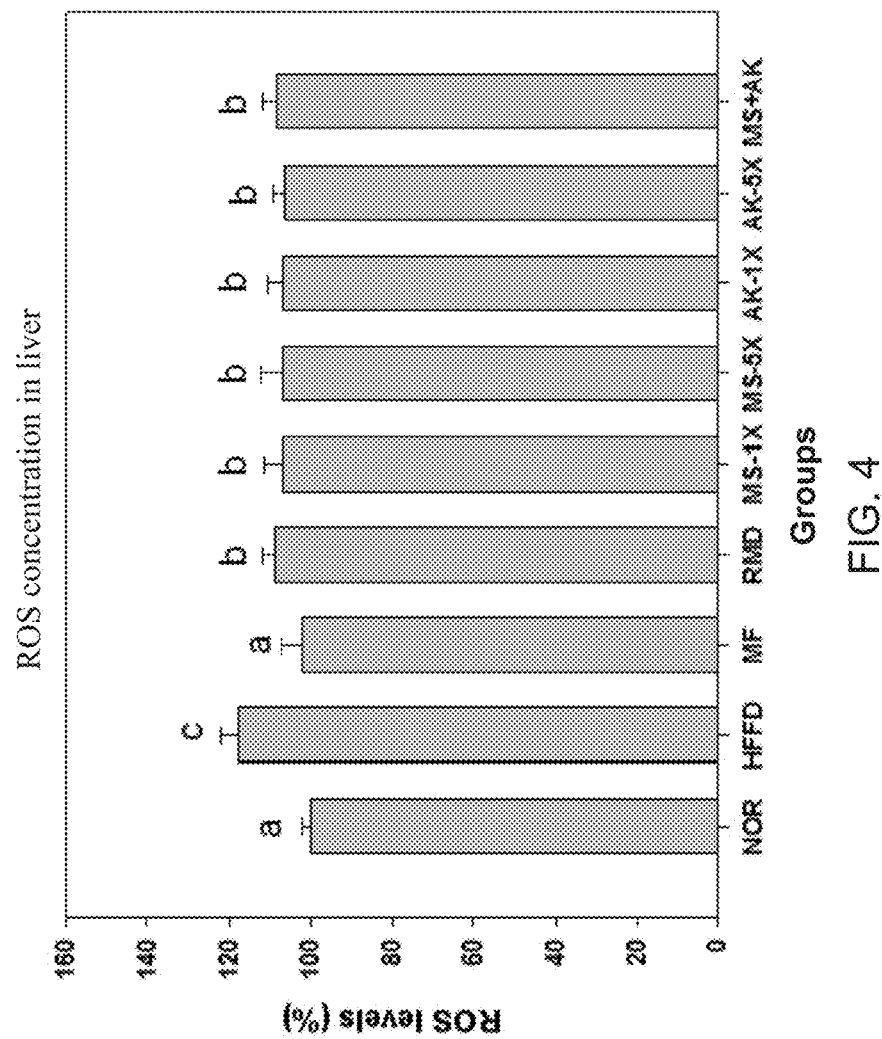
FIG. 4 shows a statistical bar graph of ROS concentration in liver.

One of key factors to induce the occurrence of diabetes mellitus and metabolism syndrome is Reactive Oxygen Species (ROS) resulted from Hyperglycemia. Please refer to FIG. 4, which provides a statistical bar graph of ROS concentration in liver. From Table FIG. 4, it can easily find that, the ROS level of the rats in HFFD group is largely higher than the ROS level of the rats in NOR group. However, comparing to the rats of HFFD group, the ROS levels of the rats in MF, RMD, MS1X, MS5X, AK1X, AK5X, and MS-AK group are largely lowered. So that, the experimental data provided by FIG. 4 prove that the Monascin and Ankaflavin indeed possess functionality to reduce the ROS concentration in liver.

Figure 5:
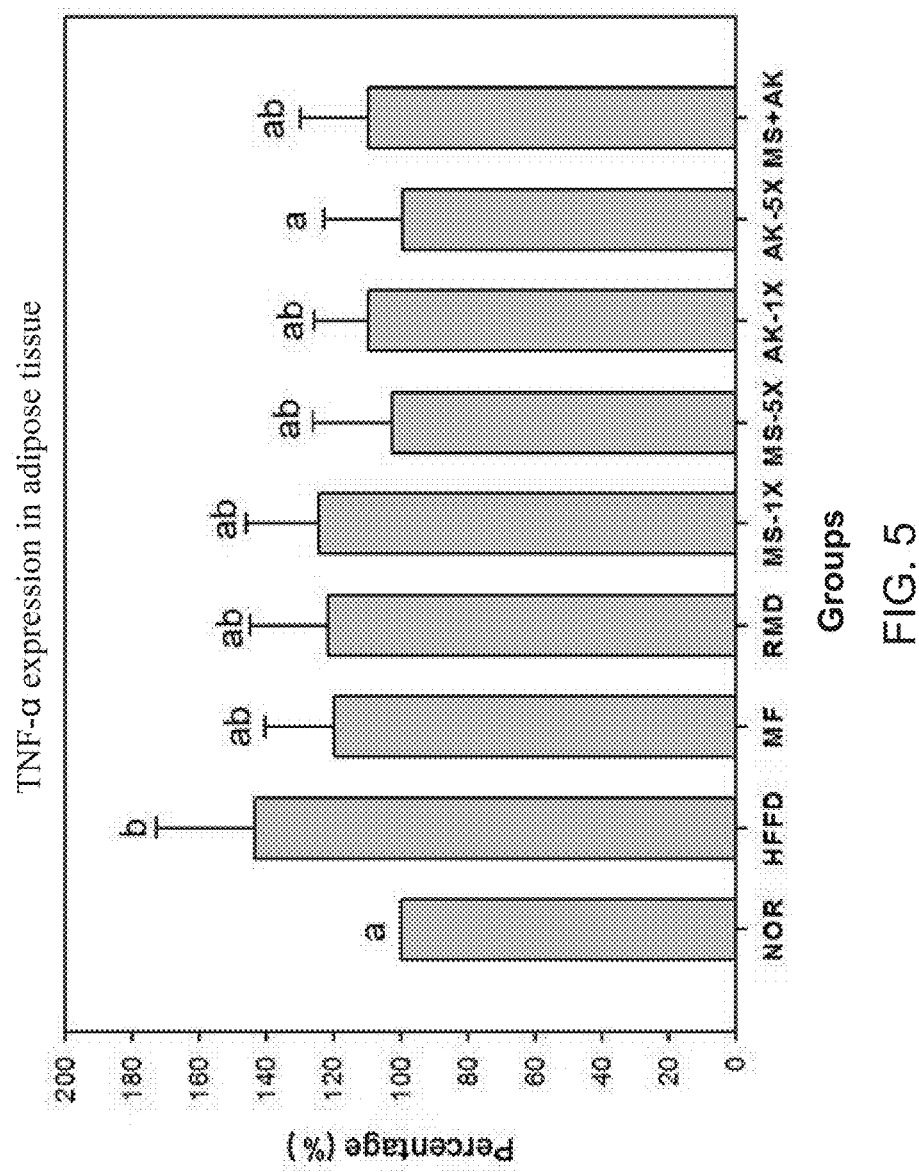
FIG. 5 shows a statistical bar graph of TNF-α expression in adipose tissue.

The adipose tissue of an obesity patient may releases inflammation factors such as hypoxia-inducible factor 1α (HIF-1α), tumor necrosis factor-α (TNF-α) and interleukin (IL), wherein the excessive amount of inflammation factors would induce lipolysis action to produce a large amount of glycerin and free fatty acid (FFA), so as to aggravate the production of Hyperglycemia, fatty liver, and high blood ketone. Please refer to FIG. 5, which provides a statistical bar graph of TNF-α expression in adipose tissue. From Table FIG. 5, it can easily find that, the percentage of TNF-α expression of the rats in HFFD group is largely higher than the percentage of TNF-α expression of the rats in NOR group. However, comparing to the rats of HFFD group, the percentages of TNF-α expression of the rats in MF, RMD, MS1X, MS5X, AK1X, AK5X, and MS-AK group are largely reduced.

Figure 6:
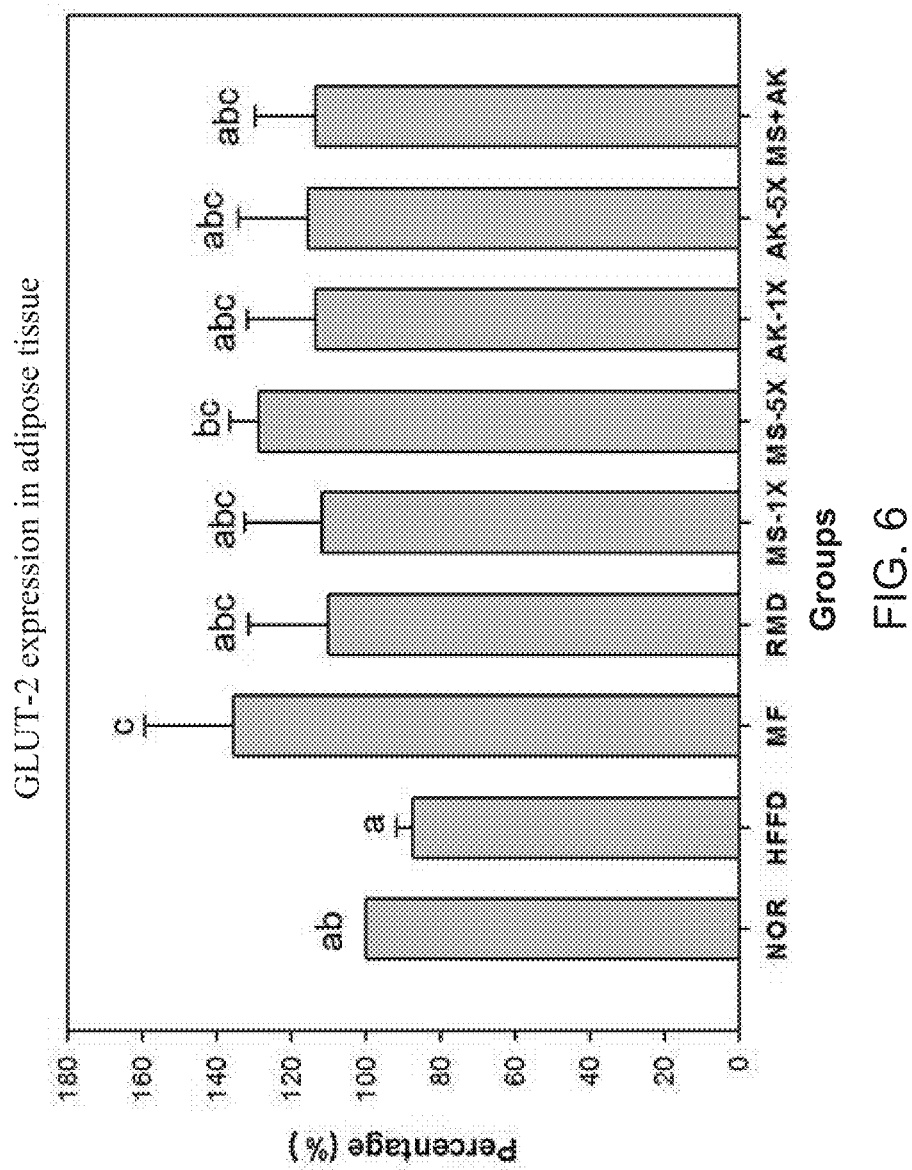
FIG. 6 shows a statistical bar graph of GLUT-2 expression in adipose tissue.
Figure 7:
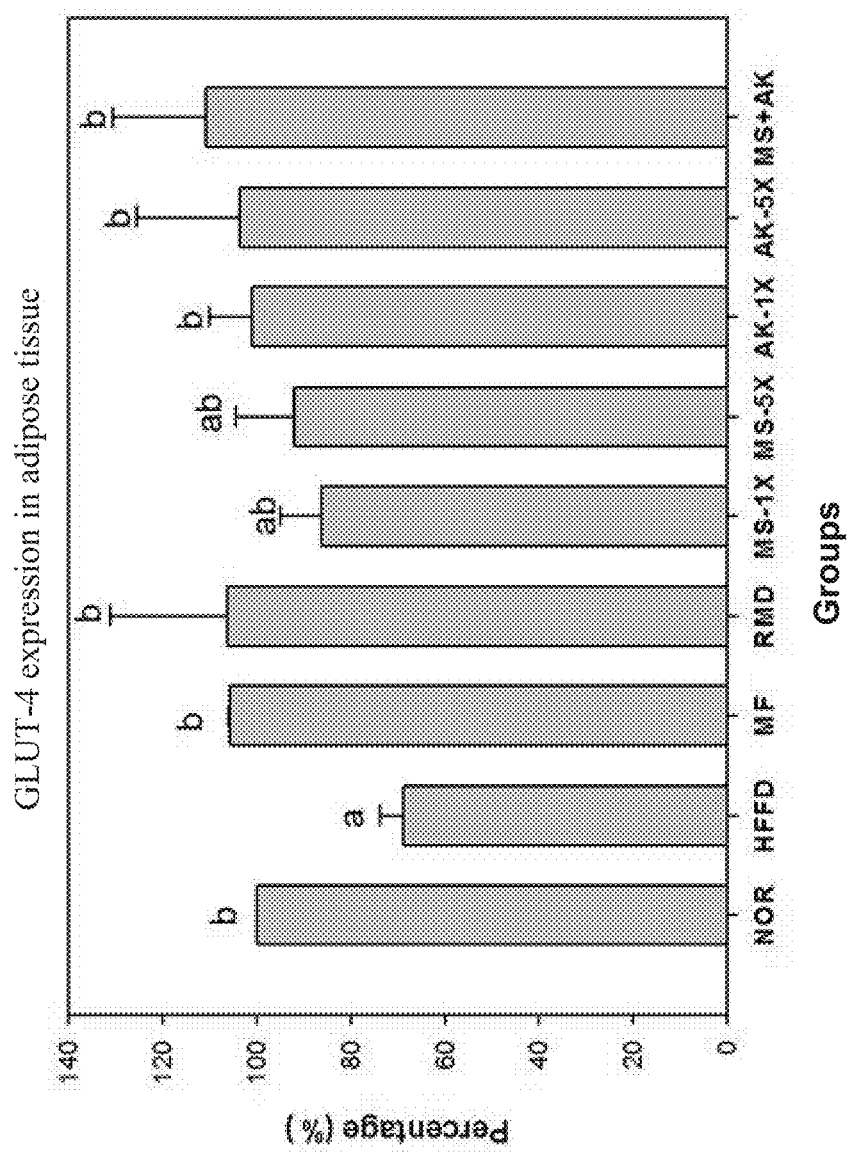
FIG. 7 shows a statistical bar graph of GLUT-4 expression in adipose tissue.

Continuously, please refer to FIG. 6 and FIG. 7, where a statistical bar graph of GLUT-2 expression in adipose tissue and a statistical bar graph of GLUT-4 expression in adipose tissue are shown. From Table FIG. 6, it can easily find that, the percentage of GLUT-2 expression of the rats in HFFD group is largely lower than the percentage of GLUT-2 expression of the rats in NOR group. However, comparing to the rats of HFFD group, the percentages of GLUT-2 expression of the rats in MF, RMD, MS1X, MS5X, AK1X, AK5X, and MS-AK group are largely enhanced. Furthermore, from Table FIG. 7, it can also find that, the percentage of GLUT-4 expression of the rats in HFFD group is largely lower than the percentage of GLUT-4 expression of the rats in NOR group. However, comparing to the rats of HFFD group, the percentages of GLUT-4 expression of the rats in MF, RMD, MS1X, MS5X, AK1X, AK5X, and MS-AK group are largely enhanced. So that, the experimental data provided by FIG. 5, FIG. 6 and FIG. 7 prove that the Monascin and Ankaflavin indeed possess functionality to enhance the GLUT (glucose transporter) expression in adipose tissue by inhibiting the expression of TNF-α.

Figure 8:
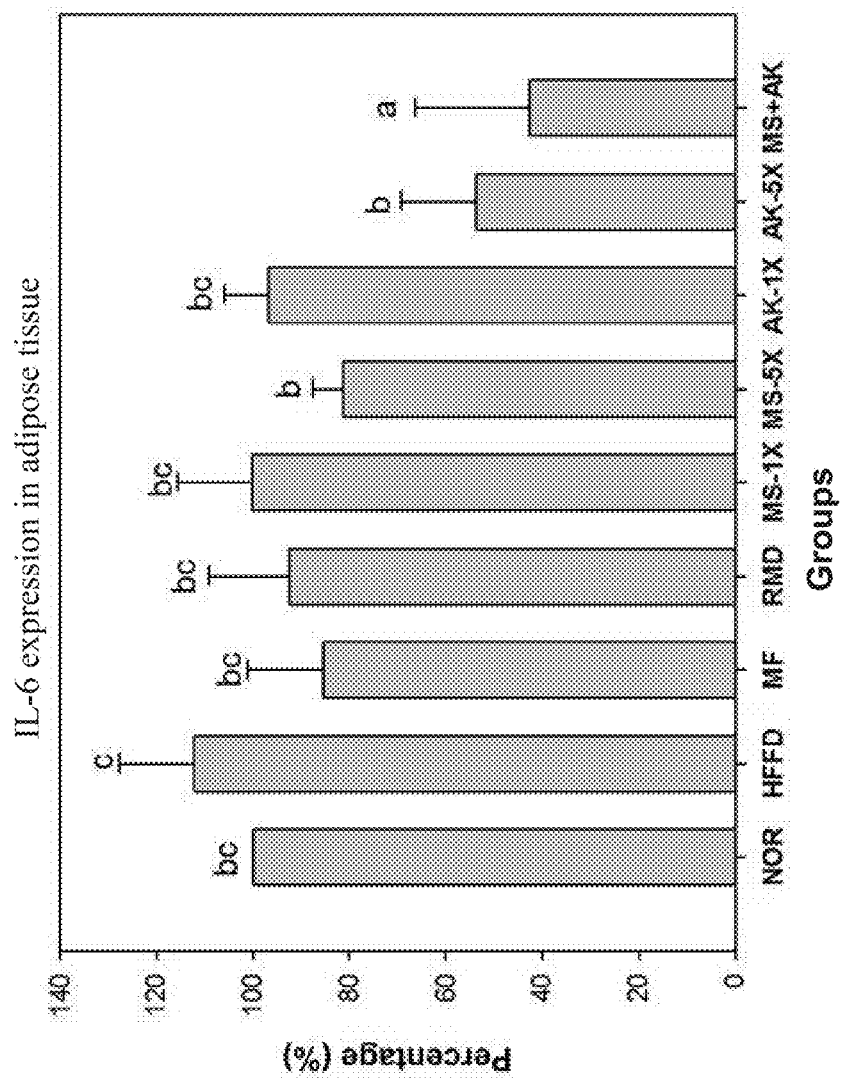
FIG. 8 shows a statistical bar graph of IL-6 expression in adipose tissue.
Figure 9:
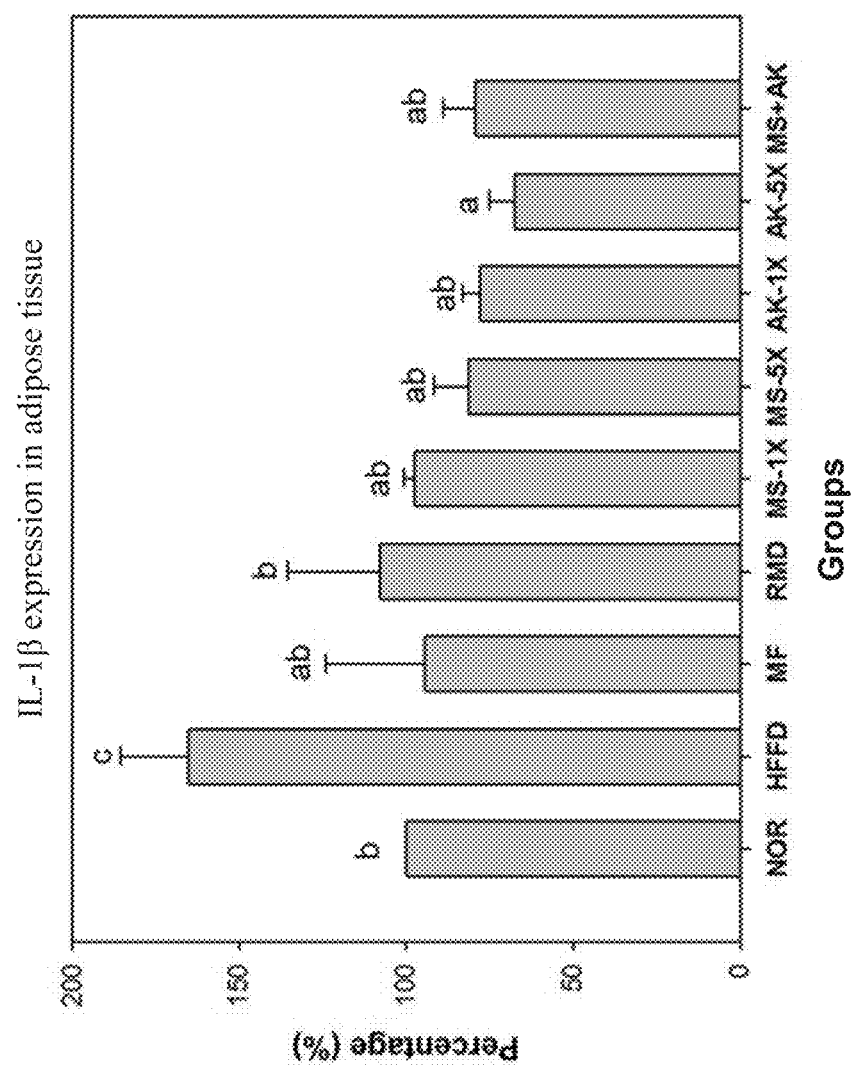
FIG. 9 shows a statistical bar graph of IL-1β expression in adipose tissue.

Please refer to FIG. 8 and FIG. 9, where a statistical bar graph of IL-6 expression in adipose tissue and a statistical bar graph of IL-1β expression in adipose tissue are provided. From Table FIG. 8, it can easily find that, the percentage of IL-6 expression of the rats in HFFD group is largely higher than the percentage of IL-6 expression of the rats in NOR group. However, comparing to the rats of HFFD group, the percentages of IL-6 expression of the rats in MF, RMD, MS1X, MS5X, AK1X, AK5X, and MS-AK group are largely lowered. Furthermore, from Table FIG. 9, it can also find that, the percentage of IL-1β expression of the rats in HFFD group is largely higher than the percentage of IL-1β expression of the rats in NOR group. However, comparing to the rats of HFFD group, the percentages of IL-1β expression of the rats in MF, RMD, MS1X, MS5X, AK1X, AK5X, and MS-AK group are largely lowered.

Figure 10:
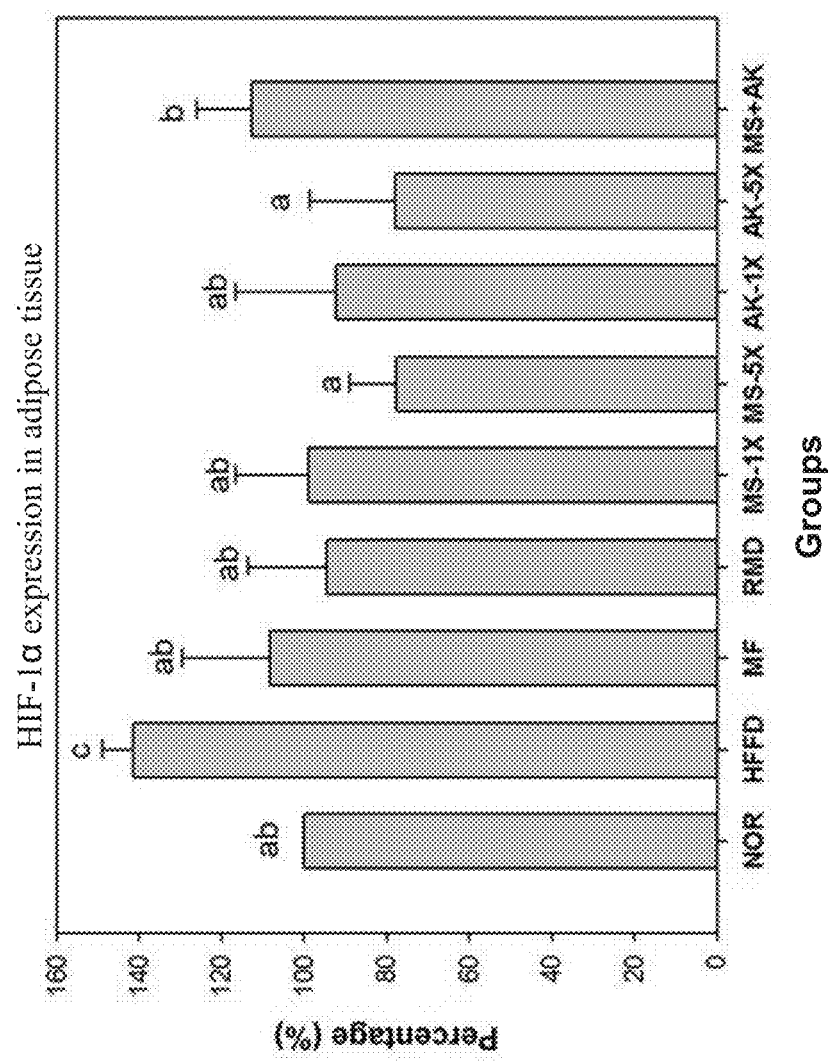
FIG. 10 shows a statistical bar graph of HIF-1α expression in adipose tissue.

Continuously, please refer to FIG. 10, which illustrates a statistical bar graph of HIF-1α expression in adipose tissue. From Table FIG. 10, it can easily find that, the percentage of HIF-1α expression of the rats in HFFD group is largely higher than the percentage of HIF-1α expression of the rats in NOR group. However, comparing to the rats of HFFD group, the percentages of HIF-1α expression of the rats in MF, RMD, MS1X, MS5X, AK1X, AK5X, and MS-AK group are largely lowered. So that, the experimental data provided by FIG. 8, FIG. 9 and FIG. 10 prove that the Monascin and Ankaflavin indeed possess functionality to reduce the ROS concentration produced in liver.

Effects Provided by Different Test Samples on Liver of SD Rats

Figure 11:
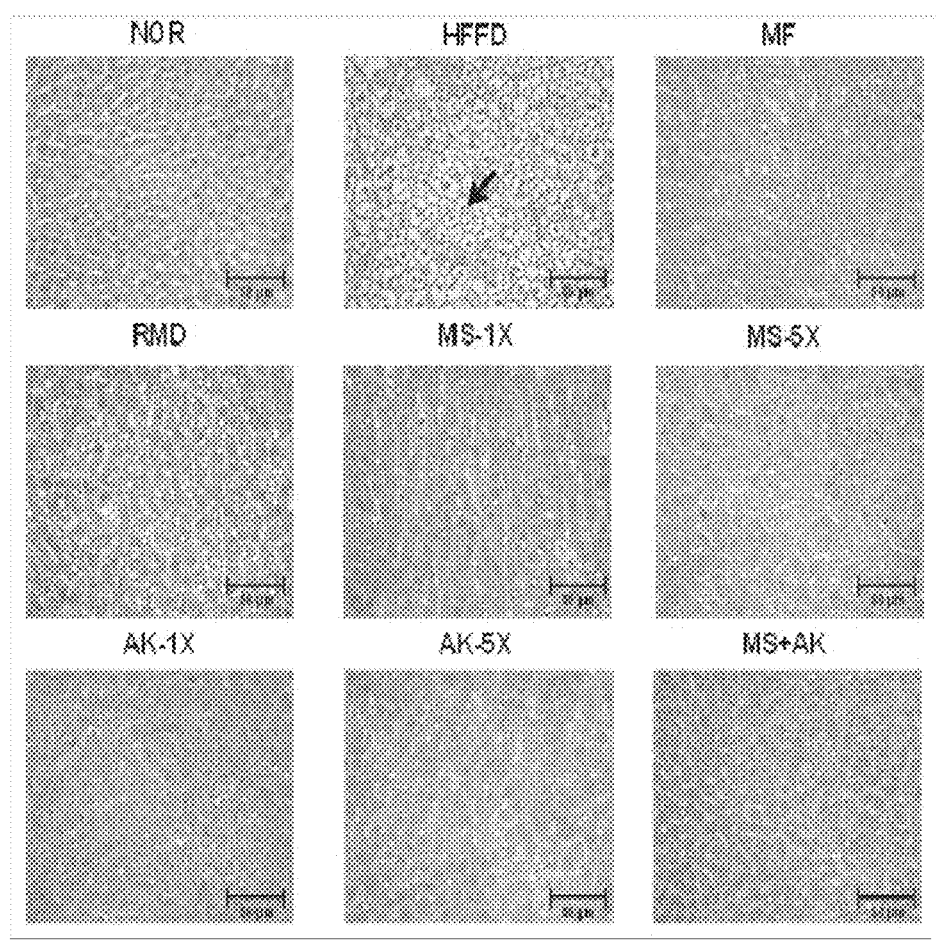
FIG. 11 shows histomorphology images of liver slices.

Liver is rich in various enzyme, such as aspartate aminotransferase (AST) and alanine aminotransferase (ALT). When liver is subjected to damage, AST and ALT would be released into blood. Please refer to FIG. 11, where histomorphology images of liver slices are provided. From FIG. 11, it can find that, the liver tissue taken out from the rats of HFFD group has become fatty liver (indicated by arrow in FIG. 11) due to excessive amount of fat accumulation. However, comparing to the rats of HFFD group, the formation of fatty liver of the rats in MF, RMD, MS1X, MS5X, AK1X, AK5X, and MS-AK group has been alleviated or solved.

Following Table 8 has recorded with AST and ALT data. From Table 8, it can easily find that, the AST and ALT levels of the rats in HFFD group are almost equal to the AST and ALT levels of the rats in NOR group. Such result implies that the liver of the hyperglycemia-induced DM rat does not be damaged. However, comparing to the rats of HFFD group, the AST and ALT levels of the rats in MF, RMD, MS1X, MS5X, AK1X, AK5X, and MS-AK group are largely lowered.

TABLE 8

| Group | AST (U/L) | ALT (U/L) |
|---|---|---|
| NOR | 71.00 ± 8.45$^b$ | 34.13 ± 2.59$^e$ |
| HFFD | 75.00 ± 11.75$^b$ | 31.88 ± 2.80$^e$ |
| MF | 71.63 ± 6.59$^b$ | 25.13 ± 3.83$^{cd}$ |
| RMD | 58.50 ± 8.98$^a$ | 24.25 ± 5.55$^d$ |
| MS1X | 61.50 ± 7.05$^a$ | 25.38 ± 2.33$^{bcd}$ |
| MS5X | 63.63 ± 5.93$^a$ | 25.50 ± 3.16$^{abc}$ |
| AK1X | 59.63 ± 4.96$^a$ | 24.75 ± 3.01$^{ab}$ |
| AK5X | 64.75 ± 11.85$^a$ | 18.88 ± 3.44$^a$ |
| MS-AK | 80.25 ± 16.22$^b$ | 31.38 ± 3.81$^e$ |

On the other hand, Hyperglycemia would also damage glomeruli of kidney, such that the metabolic wastes cannot be fully filtered out of the blood through the kidney, especially to the creatinine and urea. Following Table 9 has recorded with creatinine data. From Table 9, it can easily find that, the creatinine concentration of the rats in HFFD group is almost equal to the creatinine concentration of the rats in NOR group. However, comparing to the rats of HFFD group, the creatinine concentration of the rats in MF, RMD, MS1X, MS5X, AK1X, AK5X, and MS-AK group is largely lowered.

TABLE 9

| Group | Creatinine (mg/dL) |
|---|---|
| NOR | 0.45 ± 0.05$^{ab}$ |
| HFFD | 0.53 ± 0.07$^b$ |
| MF | 0.46 ± 0.05$^{ab}$ |
| RMD | 0.39 ± 0.10$^{ab}$ |
| MS1X | 0.50 ± 0.09$^{ab}$ |
| MS5X | 0.46 ± 0.05$^{ab}$ |
| AK1X | 0.38 ± 0.05$^{ab}$ |
| AK5X | 0.43 ± 0.09$^a$ |
| MS-AK | 0.48 ± 0.07$^{ab}$ |

Therefore, through above descriptions, the method of treatment of preventing hyperglycemia complications provided by the present invention has been introduced completely and clearly; in summary, the present invention includes the advantages of:

(1) The present invention is to provide a method of treatment of preventing hyperglycemia complications using at least one pharmaceutical made from a red mold product, wherein the red mold product is a red mold rice or a red mold *Dioscorea*, and the pharmaceutical is an extract obtained from the red mold product. Particularly, the extract can be Monascin, Ankaflavin, or a combination of Monascin and Ankaflavin. Moreover, a variety of experiment data have proved that the extract indeed exhibits a prevention effect in hyperglycemia complications comprising non-alcoholic liver damage and kidney failure.

The above description is made on embodiments of the present invention. However, the embodiments are not intended to limit scope of the present invention, and all equivalent implementations or alterations within the spirit of the present invention still fall within the scope of the present invention.

What is claimed is:

1. A method of reducing the incidence of hyperglycemia complications in a subject having a high risk of developing hyperglycemia associated non-alcoholic liver damage and kidney failure, wherein the hyperglycemia complications comprises non-alcoholic liver damage and kidney failure, said method comprising administering to the subject once-daily 3.0 mg Monascin.

2. A method of reducing the incidence of hyperglycemia complications in a subject having a high risk of developing hyperglycemia associated non-alcoholic liver damage and kidney failure, wherein the hyperglycemia complications comprises non-alcoholic liver damage and kidney failure, said method comprising administering to the subject once-daily 1.5 mg Ankaflavin.

3. A method of reducing the incidence of hyperglycemia complications in a subject having a high risk of developing hyperglycemia associated non-alcoholic liver damage and kidney failure, wherein the hyperglycemia complications comprises non-alcoholic liver damage and kidney failure, said method comprising administering to the subject once-daily a 4.5 mg composition comprising 3.0 mg Monascin and 1.5 mg Ankaflavin.

* * * * *